(12) United States Patent
Hoshi et al.

(10) Patent No.: US 9,188,530 B2
(45) Date of Patent: Nov. 17, 2015

(54) SENSOR AND IMAGE-FORMING APPARATUS

(71) Applicants: Fumikazu Hoshi, Sendai (JP); Satoru Sugawara, Sendai (JP); Toshihiro Ishii, Sendai (JP); Yoshihiro Ohba, Sendai (JP)

(72) Inventors: Fumikazu Hoshi, Sendai (JP); Satoru Sugawara, Sendai (JP); Toshihiro Ishii, Sendai (JP); Yoshihiro Ohba, Sendai (JP)

(73) Assignee: RICOH COMPANY, LTD., Tokyo (JP)

( * ) Notice: Subject to any disclaimer, the term of this patent is extended or adjusted under 35 U.S.C. 154(b) by 0 days.

(21) Appl. No.: 14/180,684

(22) Filed: Feb. 14, 2014

(65) Prior Publication Data

US 2014/0241742 A1 Aug. 28, 2014

(30) Foreign Application Priority Data

Feb. 27, 2013 (JP) ................................ 2013-036557

(51) Int. Cl.
| | |
|---|---|
| *G03G 15/00* | (2006.01) |
| *G01N 21/47* | (2006.01) |
| *B41J 11/00* | (2006.01) |
| *G01N 21/55* | (2014.01) |

(52) U.S. Cl.
CPC ............ *G01N 21/4738* (2013.01); *B41J 11/009* (2013.01); *G01N 21/474* (2013.01); *G01N 21/55* (2013.01); *G03G 15/5029* (2013.01); *G01N 2021/556* (2013.01); *G03G 2215/00616* (2013.01); *G03G 2215/00751* (2013.01)

(58) Field of Classification Search
USPC .......................... 399/38, 42, 45, 381, 388, 389
See application file for complete search history.

(56) References Cited

U.S. PATENT DOCUMENTS

| | | | |
|---|---|---|---|
| 5,699,163 | A | 12/1997 | Todoroki et al. |
| 8,185,001 | B2 * | 5/2012 | Matsumoto .................... 399/45 |
| 2003/0137679 | A1 | 7/2003 | Nakazawa et al. |
| 2005/0029474 | A1 | 2/2005 | Chun |
| 2011/0228035 | A1 | 9/2011 | Ishii et al. |
| 2011/0261139 | A1 | 10/2011 | Hoshi et al. |
| 2011/0267415 | A1 | 11/2011 | Ohba et al. |

(Continued)

FOREIGN PATENT DOCUMENTS

| | | |
|---|---|---|
| CA | 2817190 A1 | 5/2012 |
| EP | 1505454 A1 | 2/2005 |

(Continued)

OTHER PUBLICATIONS

European Search Report dated Jul. 25, 2014 in corresponding European patent application No. 14 15 5628.2.

(Continued)

*Primary Examiner* — Hoan Tran
(74) *Attorney, Agent, or Firm* — Cooper & Dunham LLP

(57) ABSTRACT

A sensor is configured to include an optical sensor including a light source and a plurality of light receivers which receive light emitted from the light source and light regularly reflected and diffusely reflected by an object, a database including output data regarding multiple objects of known and different types from the plurality of light receivers when an incident direction of light emitted from the light source forms a first direction to the object and when the incident direction of light emitted from the light source forms a second direction which is orthogonal to the first direction, and a processor which controls the light emitted from the light source to illuminate an object of unknown type and specifies the type of the object by matching the output data of the plurality of light receivers to the database.

19 Claims, 19 Drawing Sheets

(56) References Cited

U.S. PATENT DOCUMENTS

| | | |
|---|---|---|
| 2012/0134693 A1 | 5/2012 | Hoshi et al. |
| 2013/0057861 A1 | 3/2013 | Ishii et al. |
| 2013/0194573 A1 | 8/2013 | Ohba et al. |
| 2013/0216245 A1 | 8/2013 | Hoshi et al. |
| 2013/0216246 A1 | 8/2013 | Hoshi et al. |
| 2013/0216247 A1 | 8/2013 | Oba et al. |
| 2013/0228674 A1 | 9/2013 | Oba et al. |
| 2013/0235377 A1 | 9/2013 | Ishii et al. |

FOREIGN PATENT DOCUMENTS

| | | |
|---|---|---|
| JP | 7-311144 | 11/1995 |
| JP | 10-160687 | 6/1998 |
| JP | 11-249353 | 9/1999 |
| JP | 2001-140187 | 5/2001 |
| JP | 2005-156380 | 6/2005 |
| JP | 3734247 | 10/2005 |
| JP | 2006-062842 | 3/2006 |
| JP | 2012-127937 | 7/2012 |
| JP | 2012-208103 | 10/2012 |
| WO | WO 2012/070693 A1 | 5/2012 |

OTHER PUBLICATIONS

Korean official action dated Jun. 1, 2015 (and English translation thereof) in corresponding Korean Patent Application No. 10-2014-0021801.

* cited by examiner (FIRST ATTITUDE)

(SECOND ATTITUDE)

(OUTPUT LEVEL DATA OF EACH BRAND)

| TYPE | S1H | S2H | S3H | S1V | S2V | S3V |
|---|---|---|---|---|---|---|
| A | ... | ... | ... | ... | ... | ... |
| B | ... | ... | ... | ... | ... | ... |
| C | ... | ... | ... | ... | ... | ... |
| D | ... | ... | ... | ... | ... | ... |

(THIRD ATTITUDE)

(OUTPUT-LEVEL-DATA BY BRAND)

| TYPE | S1H | S2H | S3H | S1V | S2V | S3V | S1A | S2A | S3A |
|------|-----|-----|-----|-----|-----|-----|-----|-----|-----|
| A | ... | ... | ... | ... | ... | ... | ... | ... | ... |
| B | ... | ... | ... | ... | ... | ... | ... | ... | ... |
| C | ... | ... | ... | ... | ... | ... | ... | ... | ... |
| D | ... | ... | ... | ... | ... | ... | ... | ... | ... |

SENSOR AND IMAGE-FORMING APPARATUS

CROSS-REFERENCE TO RELATED APPLICATION

The present application is based on and claims priority from Japanese Patent Application No. 2013-036557, filed on Feb. 27, 2013, the disclosure of which is hereby incorporated by reference herein in its entirety.

BACKGROUND

Field of the Invention

The present invention relates to a sensor and an image-forming apparatus, and more particularly, relates to a sensor including an optical sensor and an image-forming apparatus including the sensor.

An image-forming apparatus such as a digital copier and a laser printer forms an image by transferring a toner image on a surface of a recording media such as printing paper, and fixing the image through heating and pressure under a predetermined condition. In image-formation, the heating amount and pressure upon fixing the image are considered. Especially, when high-grade image formation is required, it is necessary to set such fixing conditions individually according to the types of the recording media.

This is because the image quality on a recording media is largely affected by, for example, the types of material, thickness, humidity, smoothness, and a condition of coating thereof. For example, as for the smoothness, the fixing ratio of the toner is lowered on the concave part in the irregularity of a printing paper surface corresponding to the fixing condition. Therefore, color-unevenness occurs unless the fixing is performed under accurate conditions according to the type of the recording media.

Recently, with the progress in image-forming apparatuses and the diversity in modes of expression, there are hundreds of types of recording media at least for printing. Furthermore, in each media, there are various brands having differences in specifications such as a basis weight or thickness. In order to form a high-quality image, necessary to set a complicated fixing condition according to such brands individually.

In addition, recently, the number of brands of coated paper has increased such as plain paper, glossy coated paper, matt coated paper, and art coated paper, a plastic sheet, and emboss-coated special paper.

In a conventional image-forming apparatus, a fixing condition for printing should be set by a user. Therefore, there are complications such as the user being required to have a knowledge to distinguish a type of paper, and the user has to input the setting condition according to the type of paper every time. If the setting condition is incorrect, the image cannot be obtained optimally.

An optical detecting method which detects a brand and a surface condition of a recording media by illuminating light on the recording media and receiving reflected light and transmitted light is well-known.

For example, JP2005-156380A discloses a discriminator which discriminates a type of recording media by using reflected light and transmitted light.

JP10-160687A discloses a determiner which determines the material of a sheet according to the amount of reflected light which is reflected on the surface of the sheet-material while moving and the amount of transmitted light which is transmitted through the sheet.

JP2006-062842A discloses an image-forming apparatus including a reflective optical sensor and a determination portion. The optical sensor detects a type of recording media stored in a paper-feeding portion. The determination portion determines whether the recording media is housed in a paper-feeding portion or not, and whether the paper-feeding portion is provided or not, according to the determination output from the reflective optical sensor.

JP11-249353A discloses an image-forming apparatus including a condition-detecting portion, a high-pressure supply unit, and an output controller. The condition-detecting portion detects a plurality of polarized light components of the reflected light from recording media. The high-pressure supply unit provides a high-pressure output value so as to form an image. The output controller controls the output value of the high-pressure supply unit according to the detection result of the plurality of polarized light components by the condition-detecting portion.

JP2012-127937A discloses an optical sensor comprising an illuminating system which emits linearly polarized light in a first polarization direction to a sheet object, a first light-sensing device which is disposed on a light path of light emitted from the illuminating system and reflected regularly on the object, an optical element which transmits a linear polarization component in a second polarization direction orthogonal to the first polarization direction in the light reflected diffusely on the object, and a second light-sensing device which receives the light transmitted through the optical element.

JP3577713B discloses a measuring device comprising a light-illumination unit and a detecting unit which measures a fiber-orientation characteristic of an object to be measured. The detecting unit detects light which is nearly parallel to a light beam axis illuminated by the illumination unit and leaks from a virtual circle centering the light beam axis, so as to detect light outside a fiber of the object to be measured by being propagated in a fiber direction of the object. Then, the measuring device measures the fiber-orientation characteristic of the object according to the light detected by the detecting unit.

JP2801144B discloses a measuring device which measures a fiber orientation of paper. The measuring device comprises a projector which emits detection light of linearly polarized light to a paper-sheet surface perpendicularly and rotates the fluctuating direction of the linearly polarized light centering on the incident light axis, and a pair of light receivers which turn around the incident light axis in synchronization with the rotation of the projector and receive main linearly polarized light and sub linearly polarized light separated from reflected light.

JP3734247B discloses a determination device which determines types of recording media. The determination device comprises a first detecting unit which detects a fiber orientation of the surface of the recording media by using a plurality of light-receiving elements which receive a plurality of reflected light each having a similar reflection angle from the surface of the recording media and a different reflecting direction, a second detecting unit which detects a gloss level of the surface of the recording media by using at least one light-receiving element of the plurality or light-receiving elements, and a determination unit which determines the type of the recording media according to the detected fiber orientation and gloss level.

However, it is difficult to identify an object with high accuracy by a simple configuration.

SUMMARY

A sensor according to present invention comprises an optical sensor including a light source and a plurality of light receivers which receive light emitted from the light source and light regularly reflected and diffusely reflected by an object, a database including output data regarding multiple objects of known and different types from the plurality of light receivers when an incident direction of light emitted from the light source forms a first direction to the object and when the incident direction of light emitted from the light source forms a second direction which is orthogonal to the first direction, and a processor which controls the light emitted from the light source to illuminate an object of unknown type and specifies the type of the object by matching the output data of the plurality of light receivers to the database.

BRIEF DESCRIPTION OF THE DRAWINGS

The accompanying drawings are included to provide further understanding of the invention, and are incorporated in and constitute a part of this specification. The drawings illustrate embodiments of the invention and, together with the specification, serve to explain the principle of the invention.

DETAILED DESCRIPTION OF THE PREFERRED EMBODIMENT

Embodiment

Figure 1:
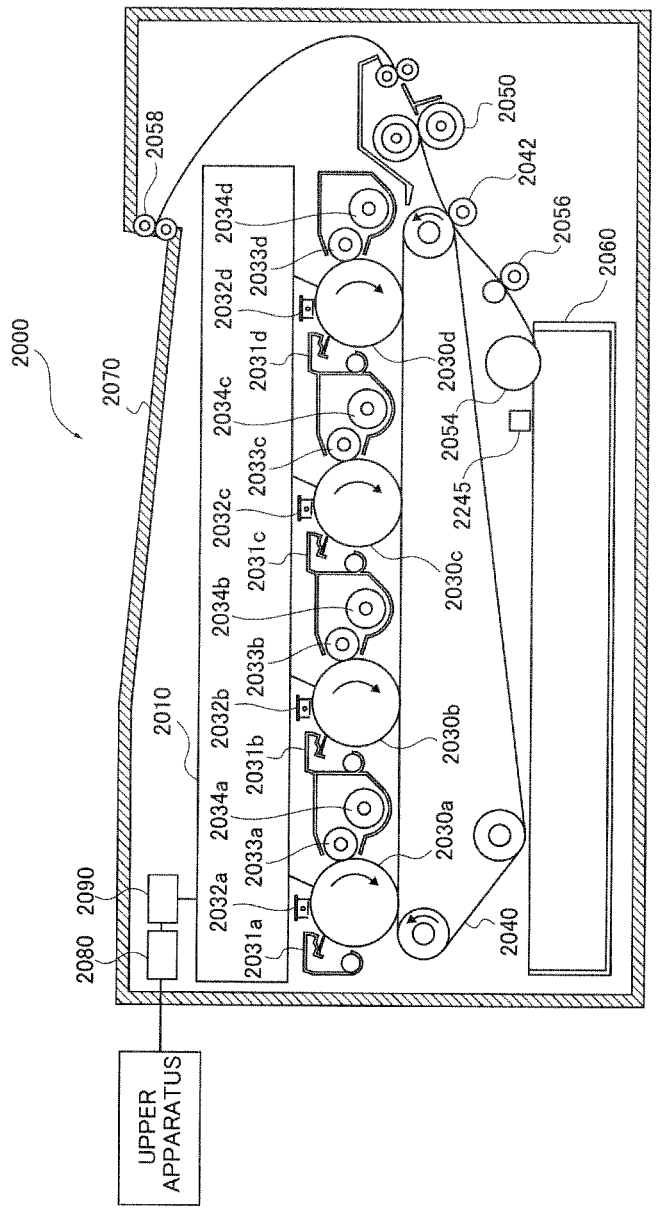
FIG. 1 provides a view schematically illustrating a configuration of a color printer according to one embodiment of the present invention.

Hereinafter, one embodiment of present invention will be described with reference to FIGS. 1-23. A configuration of a color printer 2000 according to one embodiment is shown schematically in FIG. 1.

The color printer 2000 is a multi-color printer of a tandem system which forms a full-color image by overlapping four colors (black, cyan, magenta and yellow). The color printer 2000 includes: an optical scanner 2010, four photosensitive drums 2030a, 2030b, 2030c, 2030d, four cleaning units 2031a, 2031b, 2031c, 2031d, four charging devices 2032a, 2032b, 2032c, 2032d, four developing rollers 2033a, 2033b, 2033c, 2033d, a transfer belt 2040, a transfer roller 2042, a fixing device 2050, a feeding roller 2054, a paper ejection roller 2058, a paper-feed tray 2060, a paper ejection tray 2070, a communication control device 2080, an optical sensor 2245, a sensor-driving device 2248 (omitted in FIG. 1, refer to FIGS. 11A and 11B), and a printer controller 2090 which controls each of component parts as a whole.

The communication control device 2080 controls interactive communication with an upper apparatus (personal computer, for example) through a network and so on.

The printer controller 2090 includes: a CPU; a ROM which stores a program described in CPU-readable code and various data used to execute the program; a RAM which is regarded as a memory used as a working area; an amplifier circuit; an A/D converter which converts analog data into digital data, and so on. Thus, the printer controller 2090 controls each of the component parts in response to a request sent from the upper apparatus, and sends image-information sent from the upper apparatus to the optical scanner 2010.

The photosensitive drum 2030a, the charging device 2032a, the developing roller 2033a, and the cleaning unit 2031a are used as one unit, and form an image formation station (hereinafter, referred to as "K station" for convenience) for forming a black image.

The photosensitive drum 2030b, the charging device 2032b, the developing roller 2033b, and the cleaning unit 2031b are used as one unit, and form an image formation station (hereinafter, referred to as "C station" for convenience) for forming a cyan image.

The photosensitive drum 2030c, the charging device 2032c, the developing roller 2033c, and the cleaning unit 2031c are used as one unit, and form an image formation station (hereinafter, referred to as "M station" for convenience) for forming a magenta image.

The photosensitive drum 2030d, the charging device 2032d, the developing roller 2033d, and the cleaning unit 2031d are used as one unit, and form an image formation station (hereinafter, referred to as "Y station" for convenience) for forming a yellow image.

On each surface of the photosensitive drums 2030a, 2030b, 2030c and 2030d, a photosensitive layer is formed. That is, each surface of the photosensitive drums 2030a, 2030b, 2030c and 2030d is a target to be scanned. The photosensitive drums 2030a, 2030b, 2030c, and 2030d rotate by a not-shown rotational mechanism in the directions indicated by arrows within the surfaces shown in FIG. 1.

The charging devices 2032a, 2032b, 2032c and 2032d uniformly charge surfaces of the corresponding photosensitive drums 2030a, 2030b, 2030c and 2030d, respectively.

The optical scanner 2010 scans the corresponding charged surface of the photosensitive drums 2030a, 2030b, 2030c and 2030d with light modulated for individual colors according to multi-color image information (black image information, cyan image information, magenta image information, and yellow image information) sent from the printer controller 2090. Thereby, latent images which correspond to the age information are formed on the surfaces of the photosensitive drums 2030a, 2030b, 2030c and 2030d, for each. The latent images formed herein are moved toward the directions for the corresponding developing rollers 2033a, 2033b, 2033c, and 2033d, respectively, along with the rotation of the photosensitive drums 2030a, 2030b, 2030c and 2030d.

Each of the developing rollers 2033a, 2033b, 2033c, and 2033d is applied with toner supplied from the corresponding toner cartridge (not shown in Figures) thinly and uniformly on the surface thereof, along with its rotation. Thus, when the toner on the surface of the developing roller 2033a contacts the surface of the photosensitive drum 2030a, the toner is transferred and adhered onto only the portions which are illuminated by the light. That is, the toner is adhered by the developing roller 2033a onto the latent image formed on the surface of the photosensitive drum 2030a, so as to be visualized. The image (toner image) on which the toner is adhered is moved toward the transfer belt 2040 along with the rotation of the photosensitive drum 2030a.

Toner images for yellow, magenta, cyan, and black are sequentially transferred onto the transfer belt 2040 at a predetermined timing. Thus, a multi-color image is formed by overlapping each toner image.

The paper-feed tray 2060 stores recording paper M. The feeding roller 2054 is arranged adjacent to the paper-feed tray 2060. The feeding roller 2054 picks out the recording paper one sheet at a time from the paper-feed tray 2060. The recording paper is sent out toward a gap between the transfer belt 2040 and the transfer roller 2042 at a predetermined timing. By such a configuration, the toner image on the surface of the transfer belt 2040 is transferred to the recording paper. The recording paper M, on which the toner image is transferred, is carried to the fixing device 2050.

The fixing device 2050 applies heat and pressure to the recording paper M, and the toner is fixed to the recording paper M. The recording paper M is carried to the ejection tray 2070 through the ejection roller 2058, and is stacked on the ejection tray 2070.

The cleaning unit 2031a removes residual toner on the surface of the photosensitive drum 2030a. After the residual toner is removed, the surface of the photosensitive drum 2030a returns to a position facing the charging device 2032a. The cleaning units 2031b, 2031c, and 2031d operate similar to the cleaning unit 2031a.

The optical sensor 2245 is used to specify the brand of the recording paper M housed in the paper-feed tray 2060.

Figure 2:
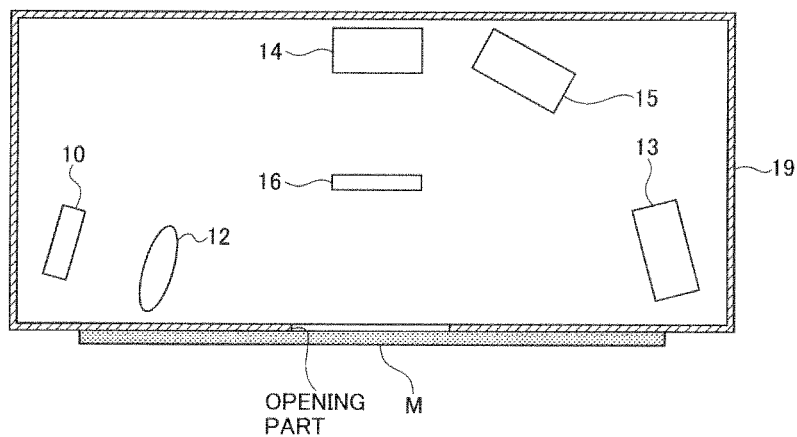
FIG. 2 provides a view illustrating a configuration of an optical sensor shown in FIG. 1.

Herein, the optical sensor 2245 includes, a light source 10, a collimate lens 12, three light receivers (13, 14 and 15), a polarizing filter 16, and a camera obscure 19 for accommodating these components as shown in FIG. 2 as an example.

The camera obscure 19 is regarded as a box member, for example, a box member made of aluminum. A black alumite-treatment is provided on the surfaces of the camera obscure 19 in order to reduce any influence due to disturbing light and stray light.

In an XYZ three-dimensional orthogonal coordinate system herein, a direction orthogonal to a surface of the recording paper M is represented as a Z-axis direction and a plane parallel to the surface of the recording paper M is represented as an XY plane. The optical sensor 2245 is arranged at the +Z side of the recording paper M.

Figure 3:
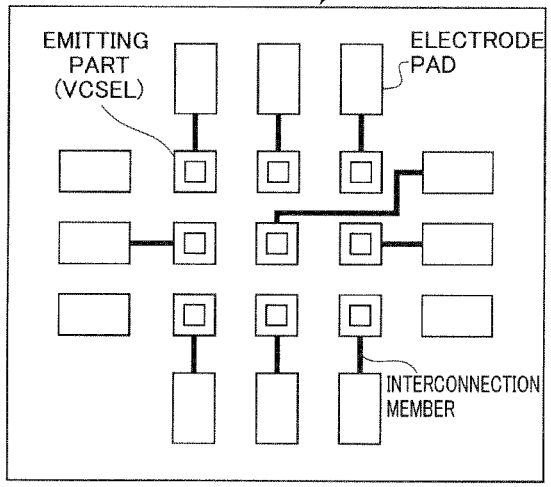
FIG. 3 provides a view illustrating a surface-emitting laser array.
Figure 4:
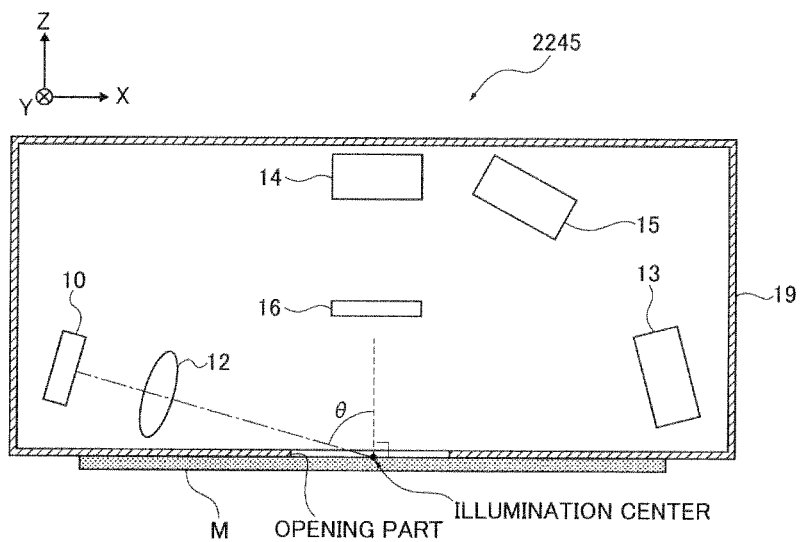
FIG. 4 provides a view illustrating an incident angle θ of light which illuminates recording paper.

The light source 10 includes a plurality of emitting elements. Each of the emitting elements is a Vertical Cavity Surface-emitting Laser. That is, the light source 10 includes a surface-emitting laser array (VCSEL array). As illustrated in FIG. 3 as an example, nine emitting elements are arranged in two dimensions.

The light source 10 is arranged so as to emit linearly polarized light of S polarization to the recording paper M. Also, an incident angle θ (refer to FIG. 4) of light from the light source 10 on the recording paper M is 80°.

The light source 10 is turned on and off through the printer controller 2090.

In FIG. 2, the collimate lens 12 is arranged on the light path of the light emitted from the light source 10, and collimates the light to be nearly parallel light. The light passing through the collimate lens 12 illuminates the recording paper M after passing through an opening part provided on the camera obscure 19. In the following, a center in an illuminated area on the surface of the recording paper M is represented as an illumination center. In addition, the light passing through the collimate lens 12 is represented as illumination light.

When the light enters an interface of a medium, a surface including the incident light and the normal line of the interface at an incident point is referred to as an "incident surface". In a case in which the incident light is formed by multiple beams, the incident surface exists for each of the multiple light beams. Accordingly, the incident surfaces of the light beams entering the illumination center are simply referred to as the incident surface of the recording paper M. That is, a plane parallel to an X-Z plane and including the illumination center is regarded as the incident surface of the recording paper M.

In the present description, not only the incident light but also reflection light which illuminates the recording paper M is described as S polarized light and/or P polarized light. The above expressions are based on the polarization direction of the incident light which illuminates the recording paper M, in order to make the description simple and reasonable. Herein, a polarization direction which is similar to that of the incident light (S polarized light) on the incident surface is referred to as the S polarized light, and a polarization direction which is perpendicular to the incident light (S polarized light) on the incident surface is referred to as the P polarized light.

The polarizing filter 16 is arranged at the +Z side of the illumination center. The polarizing filter 16 transmits the P polarized light, and shields the S polarized light. Instead of the polarizing filter 16, a polarized-light beam splitter including an equivalent function may be used.

Figure 5:
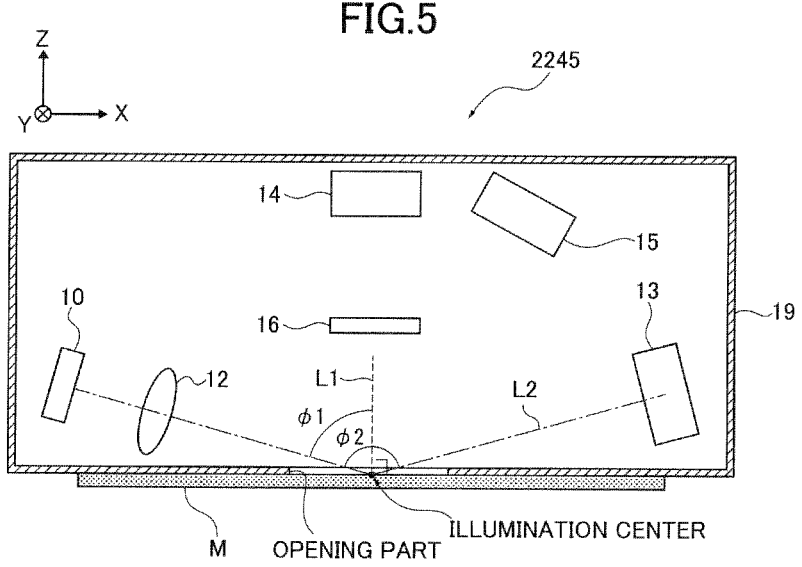
FIG. 5 provides a view illustrating a disposing position of a light receiver 13 and a light receiver 14.

The light receiver 14 is arranged at the +Z side of the polarizing filter 16 and receives the light which is transmitted through the polarizing filter 16. As illustrated in FIG. 5, an angle φ1 formed by a line L1 which connects the illumination center and the centers of the polarizing filter 16, and the light receiver 14 and the surface of the recording paper M is 90 degrees.

The light receiver 13 is arranged at the +X side of the illumination center in an X-axis direction. As illustrated in FIG. 5, an angle φ2 formed by a line L2 which connects the illumination center and the center of the light receiver 13 and the surface of the recording paper M is 170 degrees.

Figure 6:
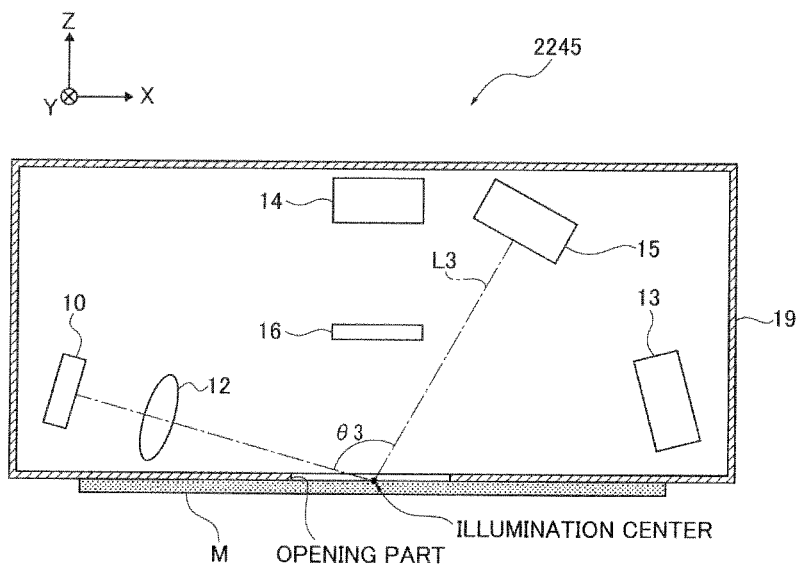
FIG. 6 provides a view illustrating a disposing position of a light receiver 15.
Figure 7A:
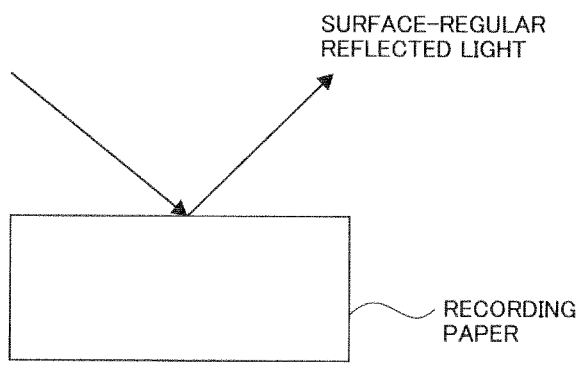
FIG. 7A provides a view illustrating surface-regular reflected light.
Figure 7B:
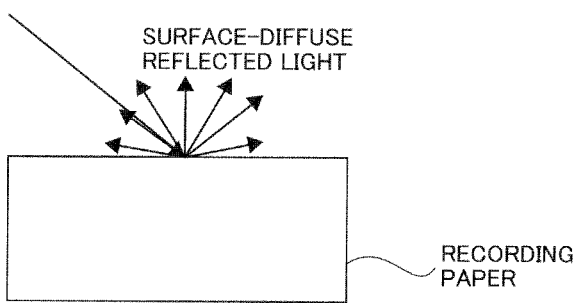
FIG. 7B provides a view illustrating surface-diffuse reflected light.
Figure 7C:
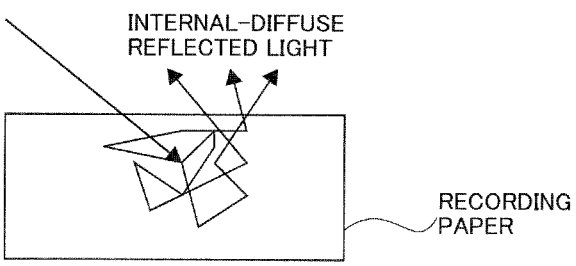
FIG. 7C provides a view illustrating internal-diffuse reflected light.

The light receiver 15 is arranged at the +X side of the illumination center in the X-axis direction. As illustrated in FIG. 6, an angle φ3 formed by a line L3 which connects the illumination center and the center of the light receiver 15 and the surface of the recording paper M is 120 degrees.

The center of the light source 10, the illumination center, the center of the polarizing filter 16, and each of the centers of the light receivers 13 to 15 exist on approximately the same plane.

The reflected light from the recording paper M when the recording paper M is illuminated may be considered to be separated into reflected light which is reflected on the surface of the recording paper M and reflected light which is reflected inside the recording paper M. In addition, the reflected light which is reflected on the surface of the recording paper M may be considered separately into regularly reflected light and diffusely reflected light. In the following, the reflected light which is reflected regularly on the surface of the recording paper M is referred to as surface-regular reflected light, and the diffusely reflected light is referred to as surface-diffuse reflected light, for convenience (refer to FIGS. 7A and 7B).

The surface of the recording paper M may be formed by flat portions and sloped portions. Smoothness of the surface of the recording paper M is determined by a ratio of the flat portions and the sloped portions. Light reflected on the flat portions becomes surface-regular reflected light and light reflected on the sloped portions becomes surface-diffuse reflected light. The surface-diffuse reflected light may be regarded as completely diffuse reflected light from the surface of the recording paper M. It can be considered that the surface-diffuse reflected light may have an isotropic nature in the reflected direction. As the smoothness increases, the amount of surface-regular reflected light increases.

On the other hand, in a case in which the recording paper M is a general purpose print sheet, reflected light from the inside of the recording paper M is diffusely reflected light alone since the reflected light from the inside of the recording paper M is multiply scattered in fabrics inside the recording paper M. In the following, the reflected light from the inside of the recording paper M may be referred to as internal-diffuse reflected light (refer to FIG. 7C), for convenience. The internal-diffuse reflected light is also, similar to the surface-diffuse reflected light, reflected light which is completely reflected diffusely from the recording paper M. It can be considered that the internal reflected light may have an isotropic nature in the reflecting direction.

The polarization direction of the surface-regular reflected light and the surface-diffuse reflected light is the same as a polarization direction of the incident light. In order to rotate the polarization directions on the surface of the recording paper M, it is required that the incident light be reflected on the surface inclined toward the rotational direction with respect to the incident direction thereof. Accordingly, the reflected light, in which the polarization direction rotates on the surface of the recording paper M, may not be reflected to either of light receiver directions, because the center of the light source 10, the illumination center, and the centers of each of the light receivers 13-15 are on the same plane.

On the other hand, the polarization direction of the internal-diffuse reflected light rotates with respect to the polarization direction of incident light. It is considered that the light inside the recording paper M may be passed through the fabric, and optically rotates while being dispersed multiply, and then, the polarization direction rotates.

Figure 8:
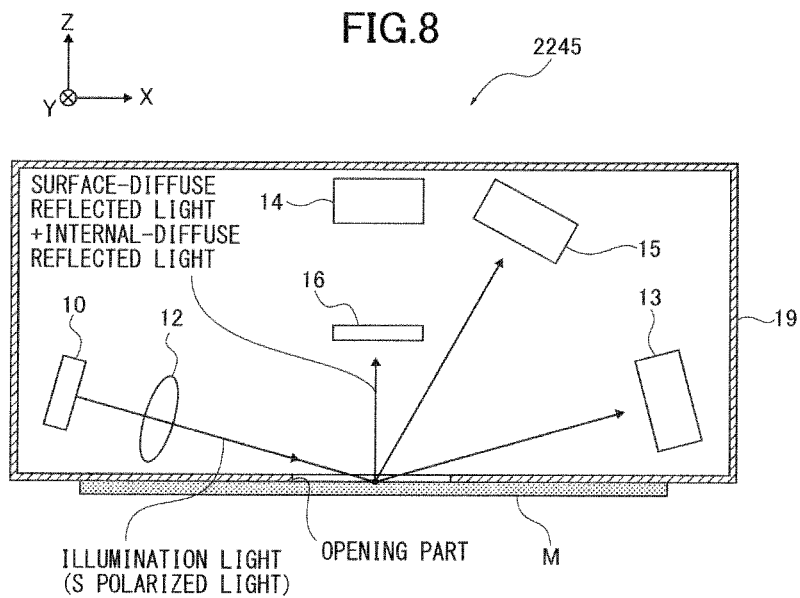
FIG. 8 provides a view illustrating reflected light which enters a polarizing filter.
Figure 9:
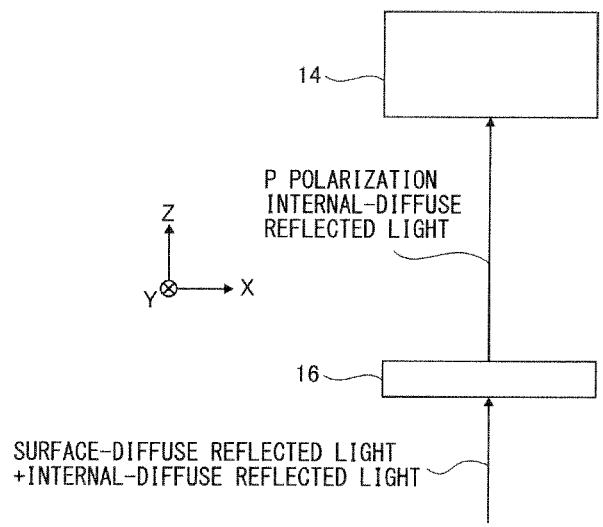
FIG. 9 provides a view illustrating light received by the light receiver 14.
Figure 10:
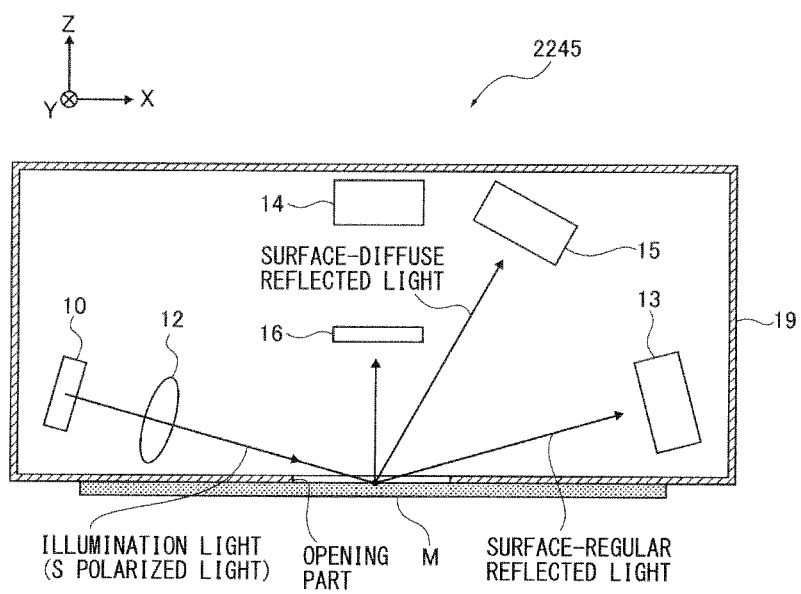
FIG. 10 provides a view illustrating light received by the light receivers 13 and 15.

Thus, the mixed reflected light of the surface-diffuse reflected light and the internal-diffuse reflected light enters the polarization filter 16 (refer to FIG. 8).

The surface-diffuse reflected light is shielded by the polarization filter 16 because it is regarded as S-polarization, similar to the incident light. On the other hand, the internal-diffuse reflected light includes S-polarization and P-polarization, so that P-polarization component is transmitted through the polarization filter 16. That is, P-polarization component included in the internal-diffuse reflected light is received by the light receiver 14 (refer to FIG. 9). In the following, P-polarization component included in the internal-diffuse reflected light is represented as P-polarization internal-diffuse reflected light, and S-polarization component included in the internal diffuse reflected light is represented as S-polarization internal-diffuse reflected light, for convenience.

The inventors have confirmed that the amount of the P-polarization internal-diffuse reflected light has a correlation with the thicknesses or the density of the recording paper M. This is because the amount of P-polarization internal-diffuse reflected light depends on the path length for the light upon passing through the fabric of the recording paper M.

The mixed light of the surface-regular reflected light, the surface-diffuse reflected light, and the internal-diffuse reflected light enters the light receiver 13. The amount of surface-diffuse reflected light and the internal diffuse reflected light is very small compared with that of the surface-regular reflected light. Thus, the amount of light received by the light receiver 13 can be regarded as the amount of surface-regular reflected light (refer to FIG. 10).

The mixed light of the surface-diffuse reflected light and the internal-diffuse reflected light enters the light receiver 15. The amount of internal-diffuse reflected light is very small compared with that of the surface-diffuse reflected light. Thus, the amount of light received by the light receiver 15 can be regarded as the light amount of the surface-diffuse reflected light (refer to FIG. 10).

Each of the light receiver 13 and the light receiver 15 outputs an electronic signal (photoelectric convertor signal) according to the amount of light received by each receiver to the printer controller 2090.

The optical sensor 2245 drives to turn around the Z-axis and moves along with the longitudinal direction of the recording paper M by the sensor-driving device 2248. Hereinafter, the longitudinal direction of the recording paper M is referred to as an L direction and the short direction of the recording paper M is referred to as a W direction.

Figure 11A:
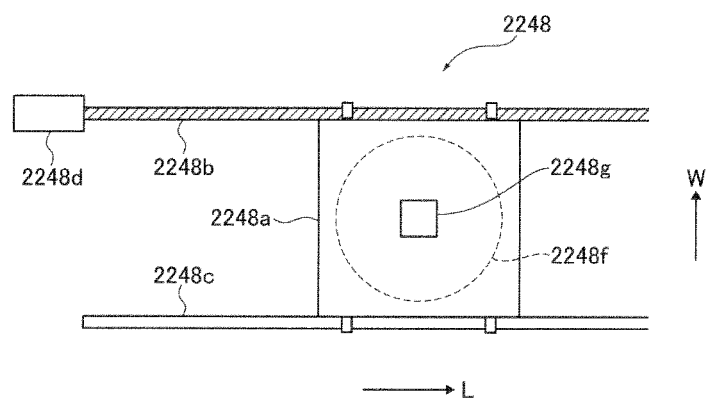
FIGS. 11A and 11B provide a view illustrating a sensor-driving device respectively.
Figure 11B:
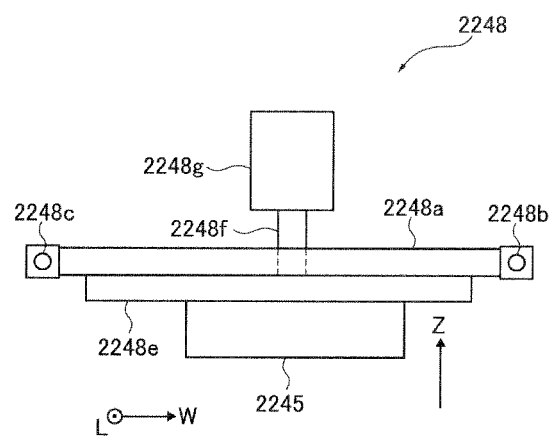

As shown in FIGS. 11A and 11B as one example, the sensor-driving device 2248 includes, a base 2248a, a shaft 2248b, a guide 2248c, a first motor 2248d, a table 2248e, a table axis 2248f, and a second motor 2248g.

The base 2248a is a plate-like ember having a rectangular shape. The base 2248a includes: in the end portion of the +W side thereof, a threaded hole in which the shaft 2248b is inserted; in the end portion of the −W side thereof, a through-hole in which the guide 2248c is inserted; and in the center portion thereof, a through-hole in which the table axis 2248f is inserted.

The shaft 2248b is a round bar having a longitudinal direction in the L direction, and a screw thread is formed on the surface thereof. The guide 2248c is a round bar having a longitudinal direction in the L direction. The shaft 2248b and the guide 2248c are arranged apart from each other in the W direction. The first motor 2248d is provided in order to rotate the shaft 2248b.

The table 2248e is a disk-shaped member. The optical sensor 2245 is attached on the −Z side surface thereof. The table axis 2248f is attached on the center of the +Z side surface of the table 2248e. The second motor 2248g is provided in order to rotate the table axis 2248f.

The first motor 2248d and the second motor 2248g drive by the printer controller 2090. When the first motor 2248d drives, the base 2248a moves along with the L direction. At the same time, the optical sensor 2245 also moves along with the L direction. When the second motor 2248g drives, the table 2248e turns around the table axis 2248f, and correspondingly, the optical sensor 2245 also turns around the Z-axis.

Figure 12A:
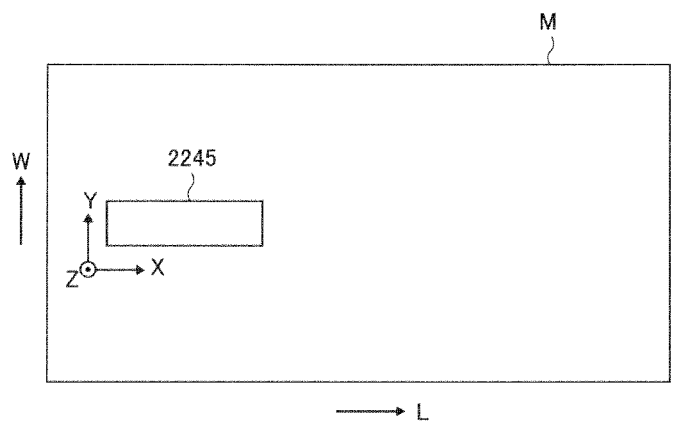
FIG. 12A provides a view illustrating a first attitude, and FIG. 12B provides a view illustrating a second attitude.
Figure 12B:
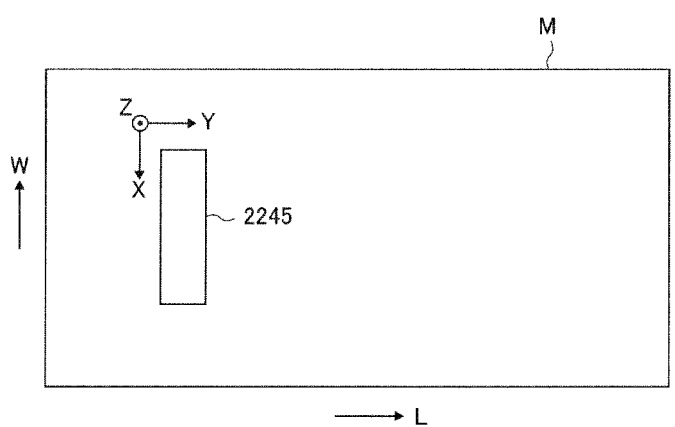
Figures 13, 14:
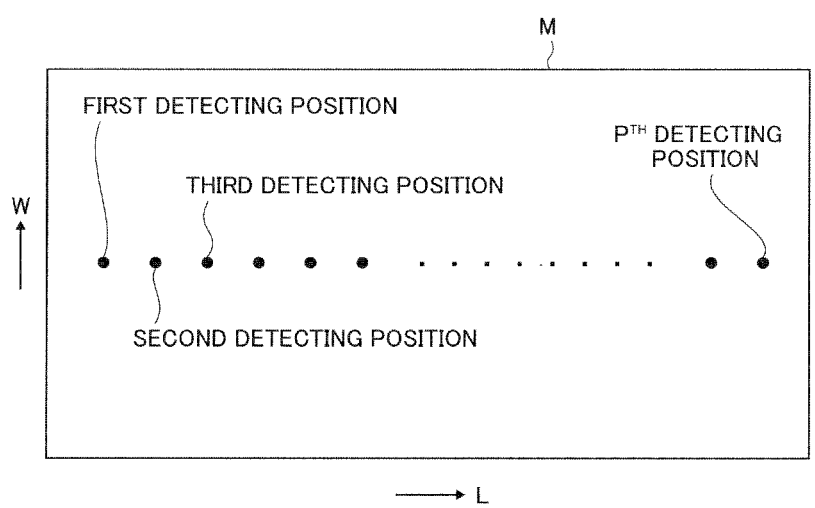
FIG. 13 provides a view illustrating output-level data by brand.
FIG. 14 provides a view illustrating P detecting positions.

As shown in FIG. 12A, the turning attitude of the optical sensor 2245 when the X-axis direction of the optical sensor 2245 and the L direction of the recording paper M are parallel to each other is represented as a "first attitude". As shown in FIG. 12B, the turning attitude of the optical sensor 2245 when the Y-axis direction of the optical sensor 2245 and the L direction of the recording paper M are parallel to each other is represented as a "second attitude".

In the present embodiment, the output levels for each of the light receivers 13-15 of the optical sensor 2245 at both of the first and second attitudes are obtained in advance so that the fibrous direction of the recording paper M of multiple brands which are suitable for the color printer 2000 is coincident with the L direction. The obtained result is stored in the ROM of the printer controller 2090 as "output level data by brand".

Herein, according to the first attitude, the output level of the light receiver 13 is represented as S1H, the output level of the light receiver 14 is represented as S2H, and the output level of the light receiver 15 is represented as S3H. According to the second attitude, the output level of the light receiver 13 is referred to as S1V, the output level of the light receiver 14 is referred to as S2V, and the output level of the light receiver 15 is referred to as S3V (refer to FIG. 13).

The printer controller 2090 performs a paper-type specifying process of recording paper M when the power of the color printer 2000 is turned on and when the recording paper M is supplied to the paper-feed tray 2060. Various processing methods can be considered as the paper-type specifying process. In the following, four processing methods (first to fourth processing methods) will be described. The different P (P is a natural number) positions in the L direction on the recording paper M are the detecting positions (refer to FIG. 14)

(First Processing Method)

Figure 15:
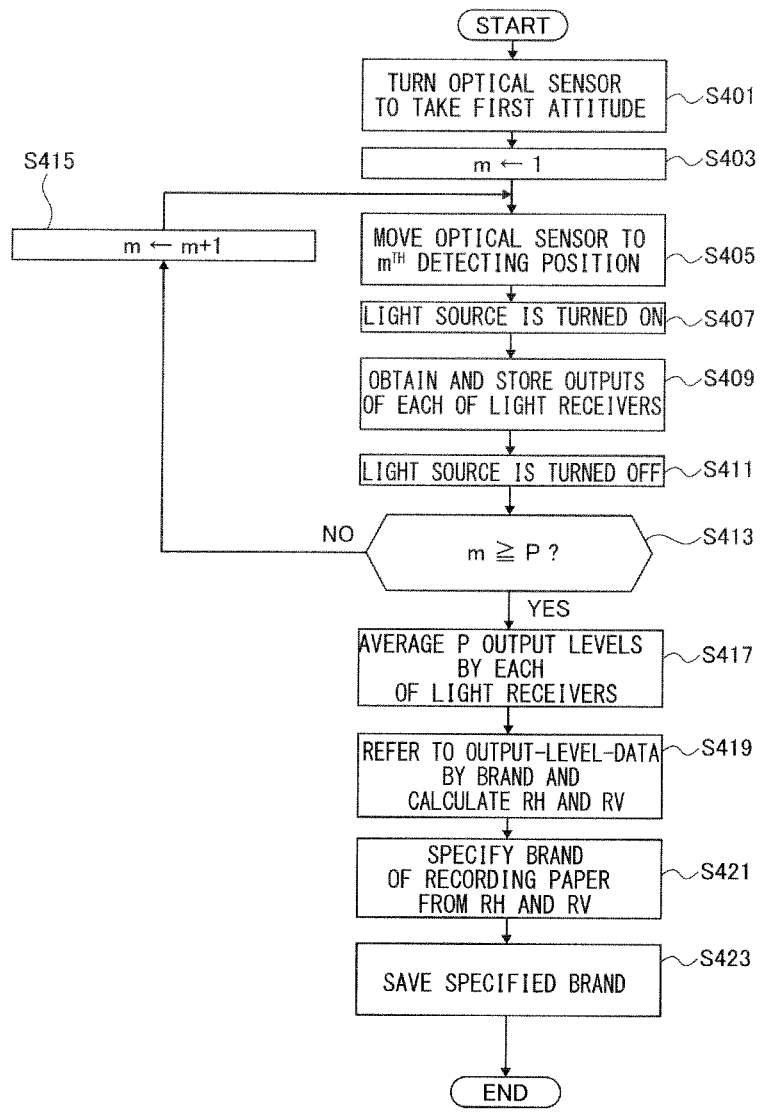
FIG. 15 provides a flowchart illustrating a first processing method.

Hereinafter, a first processing method will be described with reference to a flowchart shown in FIG. 15. The flowchart corresponds to a series of the processing algorithms performed by the CPU of the printer controller 2090 in the first processing method.

In a first step S401, the optical sensor 2245 turns so as to take the first attitude through the sensor-driving device 2248.

In a next step S403, a starting value 1 is set to a variable number m where a value for specifying a detecting position is stored.

In a next step S405, the optical sensor 2245 moves to the $m^{th}$ detecting position through the sensor-driving device 2248.

In the next step S407, the light source 10 of the optical sensor 2245 is turned on.

In the next step S409, output signals of each of the light receivers 13-15 are obtained and stored in the RAM.

In the next step S411, the light source 10 of the optical sensor 2245 is turned off.

In the next step S413, it is determined whether the value of the variable number m is P or more. When the value of the variable number m is less than P, the determination herein is rejected and the process proceeds with a step S415.

In the step S415, the variable number m is added 1 (+1), and the process goes back to the above step S405.

The steps S405 to S415 are continuously repeated until the determination in the step S413 is accepted.

When the variable number m becomes P or more, the determination in the step S413 is accepted and the process proceeds with a step S417.

In the step S417, the P output levels are averaged in each of the light receivers 13-15. An average value of the output level in the light receiver 13 is referred to as S1', an average value of the output level in the light receiver 14 is referred to as S2', and an average value of the output level in the light receiver 15 is referred to as S3'.

In the next step S419, with reference to the output level data of each brand stored in the ROM of the printer controller 2090, a precision ratio RH is calculated by the following formula 1, and a precision ratio RV is calculated by the following formula 2, regarding each brand.

$$RH = \left(1 - \left|\frac{S1H - S1'}{S1H + S1'}\right|\right) \times \left(1 - \left|\frac{S2H - S2'}{S2H + S2'}\right|\right) \times \left(1 - \left|\frac{S3H - S3'}{S3H + S3'}\right|\right) \quad (1)$$

$$RV = \left(1 - \left|\frac{S1V - S1'}{S1V + S1'}\right|\right) \times \left(1 - \left|\frac{S2V - S2'}{S2V + S2'}\right|\right) \times \left(1 - \left|\frac{S3V - S3'}{S3V + S3'}\right|\right) \quad (2)$$

In the next step S421, according to the calculated precision ratio RH and precision ratio RV by brand, the brand having a maximum ratio in one of the precision ratio RH and precision ratio RV is extracted. Thus, the extracted brand is regarded as the brand of the recording paper M.

In the next step S423, the specified brand of the recording paper M is saved in the RAM. Then, the first processing method ends.

(Second Processing Method)

Figure 16:
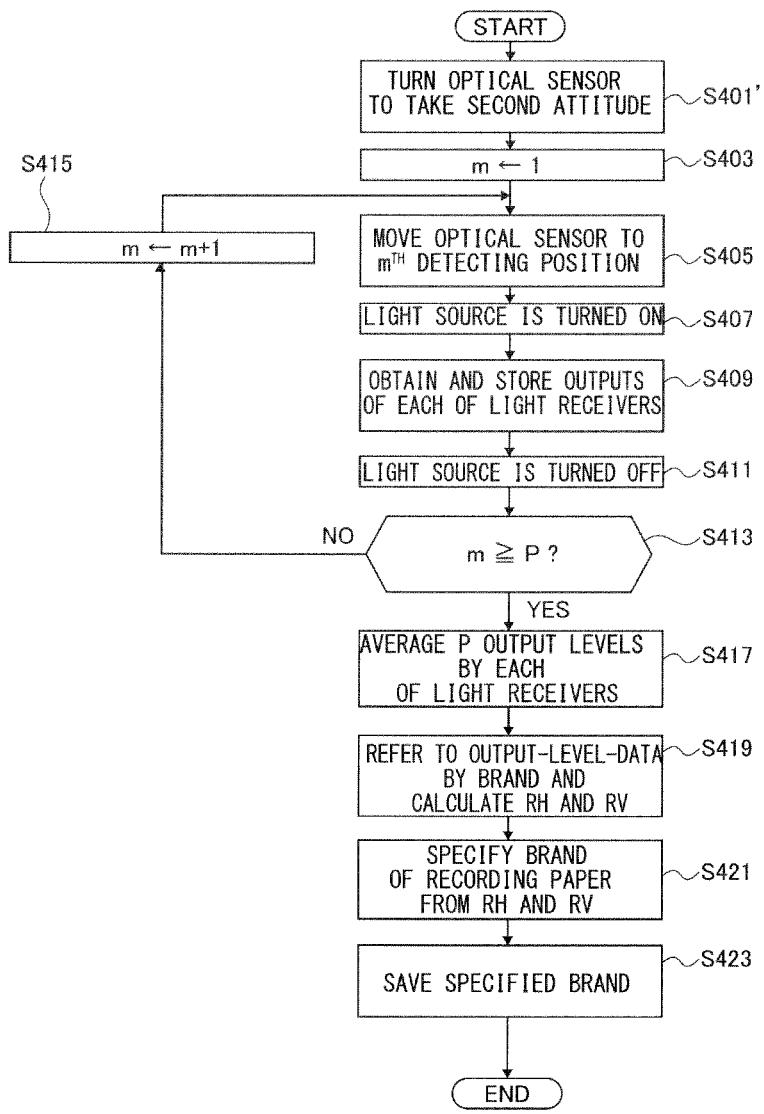
FIG. 16 provides a flowchart illustrating a second processing method.

Hereinafter, a second processing method will be described with reference to a flowchart shown in FIG. 16. The flowchart corresponds to a series of the processing algorithms performed by the CPU of the printer controller 2090 in the second processing method.

The second processing method includes the steps similar to those in the first processing method, except that the step S401 in the first processing method is replaced with a step S401'.

In the step S401', the optical sensor 2245 turns so as to take the second attitude through the sensor-driving device 2248. The succeeding steps are similar to those in the first processing method.

That is, the second processing method is different from the first processing method only in the attitude of the optical sensor 2245.

(Third Processing Method)

Figure 17:
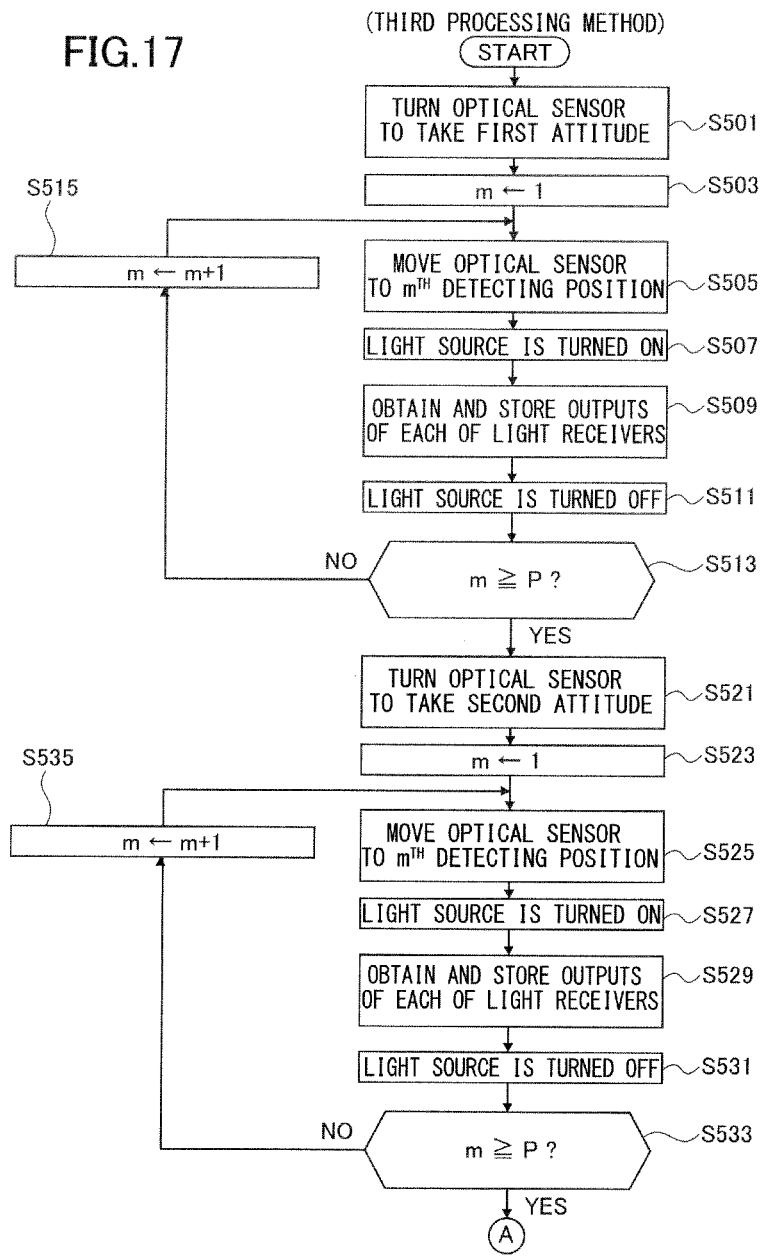
FIGS. 17 and 18 provide a flowchart illustrating a third processing method.
Figure 18:
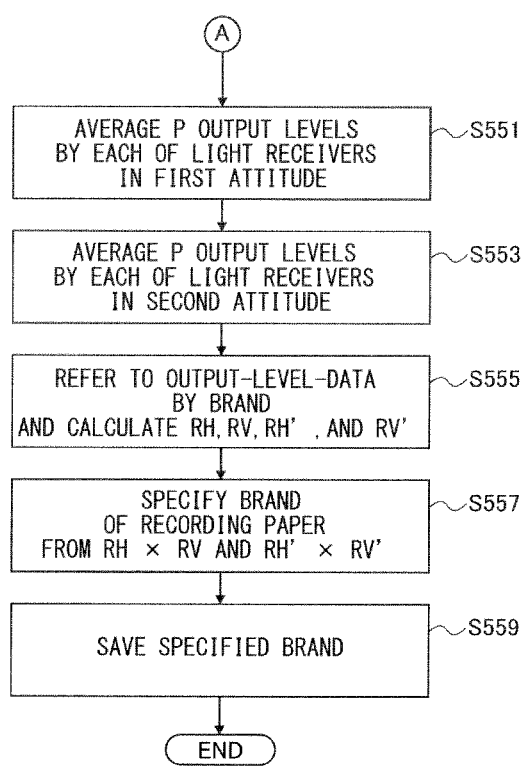

Hereinafter, a third processing method will be described with reference to a flowchart shown in FIGS. 17-18. The flowchart corresponds to a series of processing algorithms performed by the CPU of the printer controller 2090 in the third processing method.

In the first step S501, the optical sensor 2245 turns so as to take the first attitude through the sensor-driving device 2248.

In the next step S503, a starting value 1 is set to a variable number m where a value for specifying a detecting position is stored.

In the next step S505, the optical sensor 2245 moves to the $m^{th}$ detecting position through the sensor-driving device 2248.

In the next step S507, the light source 10 of the optical sensor 2245 is turned on.

In the next step S509, output signals of each of the light receivers 13-15 are obtained and stored in the RAM.

In the next step S511, the light source 10 of the optical sensor 2245 is turned off.

In the next step S513, it is determined whether the value of the variable number m is P or more. When the value of the variable number m is less than P, the determination herein is rejected and the process proceeds with a step S515.

In the step S515, the variable number m is added 1 (+1), then the process goes back to the above step S505.

The steps S505 to S515 are repeated continuously until the determination in the step S513 is accepted.

When the variable number m becomes P or more, the determination in the step S513 is accepted and the process proceeds with a step S521.

In the step S521, the optical sensor 2245 turns so as to take the second attitude through the sensor-driving device 2248.

In the next step S523, a starting value 1 is set to a variable number m where a value for specifying a detecting position is stored.

In the next step S525, the optical sensor 2245 moves to the detecting position through the sensor-driving device 2248.

In the next step S527, the light source 10 of the optical sensor 2245 is turned on.

In the next step S529, output signals of each of the light receivers 13-15 are obtained and stored in the RAM.

In the next step S531, the light source 10 of the optical sensor 2245 is turned off.

In the next step S533, it is determined whether the value of the variable number m is P or more. When the value of the variable number m is less than P, the determination herein is rejected and the process proceeds with a step S535.

In the step S535, the variable number m is added 1 (+1), then, the process goes back to the above step S525.

The steps S525 to S535 are continuously repeated until the determination in the step S533 is accepted.

When the variable number m becomes P or more, the determination in the step S533 is accepted and the process proceeds with a step S551.

In the step S551, the P output levels in each of the light receivers 13-15 while the optical sensor 2245 is at the first attitude are averaged. An average value of the output level in the light receiver 13 is referred to as S1H', an average value of the output level in the light receiver 14 is referred to as S2H', and an average value of the output level in the light receiver 15 is referred to as S3H'.

In the next step S553, the P output levels for each of the light receivers 13-15 while the optical sensor 2245 is at the second attitude are averaged. An average value of the output level in the light receiver 13 is referred to as S1V', an average value of the output level in the light receiver 14 is referred to as S2V', and an average value of the output level in the light receiver 15 is referred to as S3V'.

In the next step S555, with reference to the output level data of each brand stored in the ROM of the printer controller 2090, a precision ratio RH is calculated by the following formula 3, a precision ratio RV is calculated by the following formula 4, a precision ratio RH' is calculated by the following formula 5, and a precision ratio RV' is calculated by the following formula 6, regarding each brand.

$$RH = \left(1 - \left|\frac{S1H - S1H'}{S1H + S1H'}\right|\right) \times \left(1 - \left|\frac{S2H - S2H'}{S2H + S2H'}\right|\right) \times \left(1 - \left|\frac{S3H - S3H'}{S3H + S3H'}\right|\right) \quad (3)$$

$$RV = \left(1 - \left|\frac{S1V - S1V'}{S1V + S1V'}\right|\right) \times \left(1 - \left|\frac{S2V - S2V'}{S2V + S2V'}\right|\right) \times \left(1 - \left|\frac{S3V - S3V'}{S3V + S3V'}\right|\right) \quad (4)$$

$$RH' = \left(1 - \left|\frac{S1H - S1V'}{S1H + S1V'}\right|\right) \times \left(1 - \left|\frac{S2H - S2V'}{S2H + S2V'}\right|\right) \times \left(1 - \left|\frac{S3H - S3V'}{S3H + S3V'}\right|\right) \quad (5)$$

$$RV' = \left(1 - \left|\frac{S1V - S1H'}{S1V + S1H'}\right|\right) \times \left(1 - \left|\frac{S2V - S2H'}{S2V + S2H'}\right|\right) \times \left(1 - \left|\frac{S3V - S3H'}{S3V + S3H'}\right|\right) \quad (6)$$

In the next step S557, according to the calculated precision ratios RH, RV, RH' and RV' by brand, a brand having a maximum ratio in one of the precision ratio RH×RV and the precision ratio RH'×RV' is extracted. Thus, the extracted brand is regarded as the brand of the recording paper M.

In the next step S559, the specified brand of the recording paper M is saved in the RAM. Thus, the third processing method ends.

(Fourth Processing Method)

Figure 19:
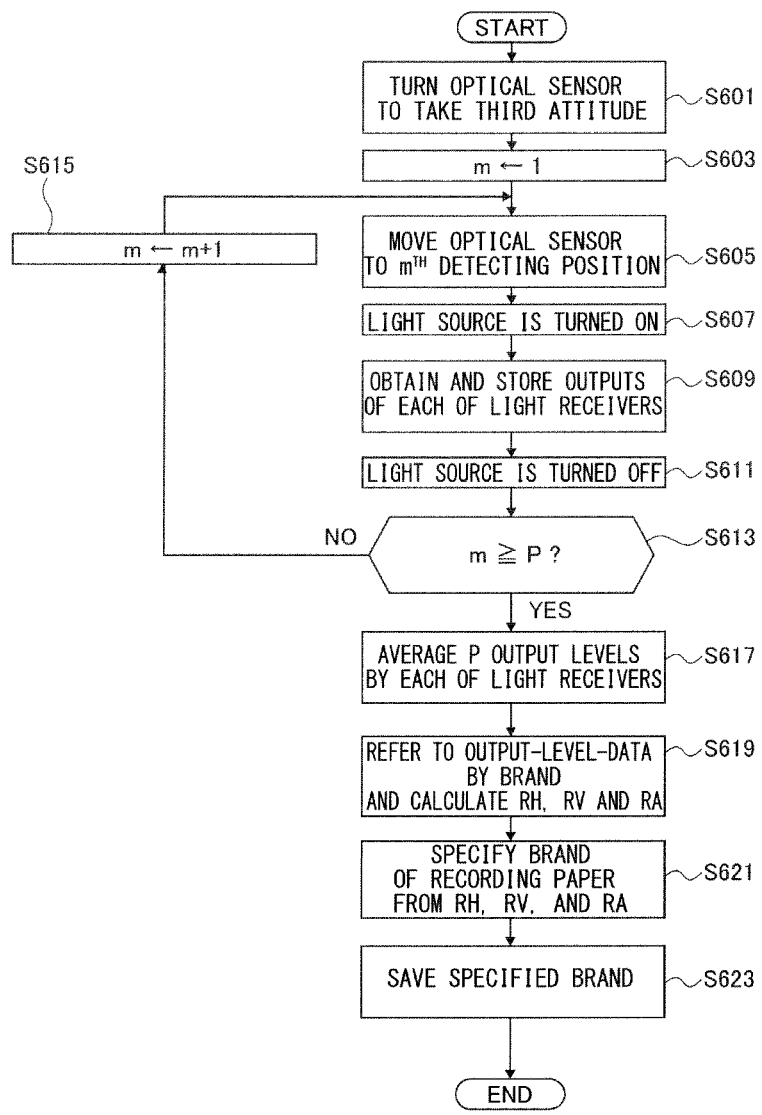
FIG. 19 provides a flowchart illustrating a fourth processing method.
Figures 20, 21:
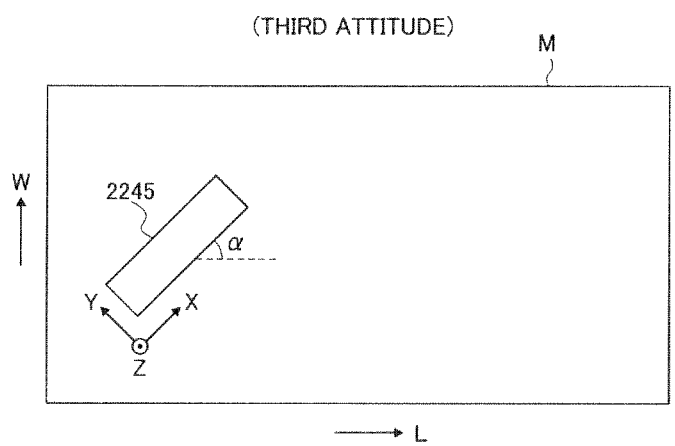
FIG. 20 provides a view illustrating a third attitude.
FIG. 21 provides a view illustrating output-level data by brand in the fourth processing method.

Hereinafter, a fourth processing method will be described with reference to a flowchart shown in FIG. 19. The flowchart corresponds to a series of processing algorithms performed by the CPU of the printer controller 2090 in the fourth processing method. As shown in FIG. 20, a third attitude is defined such as a turning attitude of the optical sensor 2245 when the angle formed by the X-axis direction of the optical sensor 2245 and the direction of the recording paper M is 0<α<90. In addition, the output level data of each brand includes an output level S1A of the light receiver 13, an output level S2A of the light receiver 14, and the output level S3A of the light receiver 15 when the optical sensor 2245 is at the third attitude (refer to FIG. 21). As an example herein, α=45 degrees but it is not limited to the above.

In the first step S601, the optical sensor 2245 turns so as to take the third attitude through the sensor-driving device 2248.

In the next step S603, a starting value 1 is set to a variable number m where a value for determining a detecting position is stored.

In a next step S605, the optical sensor 2245 is moved to the $m^{th}$ detecting position through the sensor-driving device 2248.

In the next step S607, the light source 10 of the optical sensor 2245 is turned on.

In the next step S609, output signals of each of the light receivers 13-15 are obtained and stored in the RAM.

In the next step S611, the light source 10 of the optical sensor 2245 is turned off.

In the next step S613, it is determined whether the value of the variable number m is P or more. When the value of the variable number m is lower than P, the determination herein is rejected and the process proceeds to a step S615.

In the step S615, the variable number m is added 1 (+1), then, the process goes back to the above step S605.

The steps S605 to S615 are continuously repeated until the determination in the step S613 is accepted.

When the variable number m becomes P or more, the determination in the step S613 is accepted and the process proceeds with a step S617.

In the step S617, the output level of P is averaged for each of the light receivers. The average value of the output level in the light receiver 13 is referred to as S1", the average value of the output level in the light receiver 14 is referred to as S2", and the average value of the output level in the light receiver 15 is referred to as S3".

In the next step S619, with reference to the output level data by brand stored in the ROM of the printer controller 2090, a precision ratio RH is calculated by using the following formula 7, a precision ratio RV is calculated by using the following formula 8, and a precision ratio RA is calculated by using the following formula 9, regarding each brand.

$$RH = \left(1 - \left|\frac{S1H - S1''}{S1H + S1''}\right|\right) \times \left(1 - \left|\frac{S2H - S2''}{S2H + S2''}\right|\right) \times \left(1 - \left|\frac{S3H - S3''}{S3H + S3''}\right|\right) \quad (7)$$

$$RV = \left(1 - \left|\frac{S1V - S1''}{S1V + S1''}\right|\right) \times \left(1 - \left|\frac{S2V - S2''}{S2V + S2''}\right|\right) \times \left(1 - \left|\frac{S3V - S3''}{S3V + S3''}\right|\right) \quad (8)$$

$$RA = \left(1 - \left|\frac{S1A - S1''}{S1A + S1''}\right|\right) \times \left(1 - \left|\frac{S2A - S2''}{S2A + S2''}\right|\right) \times \left(1 - \left|\frac{S3A - S3''}{S3A + S3''}\right|\right) \quad (9)$$

In the next step S621, regarding the calculated precision ratios RH, RV and RA by brand, a brand having a maximum ratio in one of the precision RH, RV and RA is extracted. Thus, the extracted brand is regarded as the brand of the recording paper M.

In the next step S623, the extracted brand of the recording paper M is saved in the RAM. Thus, the fourth processing method ends.

When receiving a job-request for print by a user, the printer controller 2090 reads out the information of the brand of the recording paper M saved in the RAM, and determines the conditions which are the most suitable for development and transfer for the brand of the recording paper M from the development and transfer table.

Thus, the printer controller 2090 controls a developing device and a transfer device for each of the station according to the most suitable developing condition and transfer condition. For example, a transfer voltage and a toner quantity may be controlled. By this configuration, a high quality image can be formed on the recording paper M.

Figure 22:
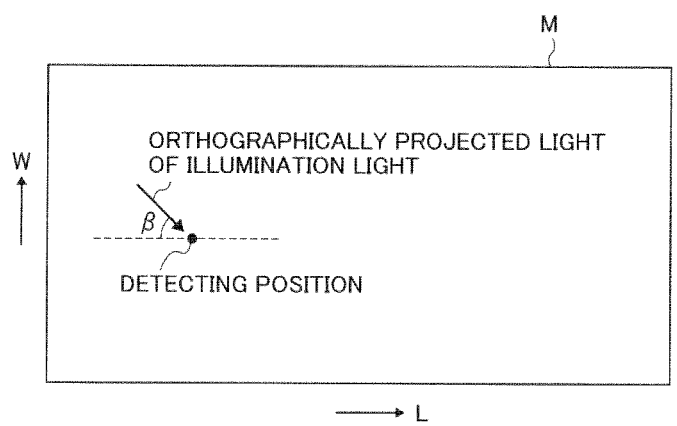
FIG. 22 provides a view illustrating an angle β.

On the other hand, due to the manufacturing process, the recording paper M includes an orientation in fabric which constitutes the recording paper M. The fabric orientation may be also referred to as a fibrous direction, and formed to be along with the fibrous direction of the recording paper M during the manufacturing process. Thus, even if in the same brand of recording paper, the reflecting characteristics may differ when the incident directions of illumination light are different for each. Herein, as shown in FIG. 22, an angle formed by the incident direction of illumination light when the light is orthographically projected on the plane perpendicular to the surface of the recording paper M and the L direction is represented as β°.

Figure 23:
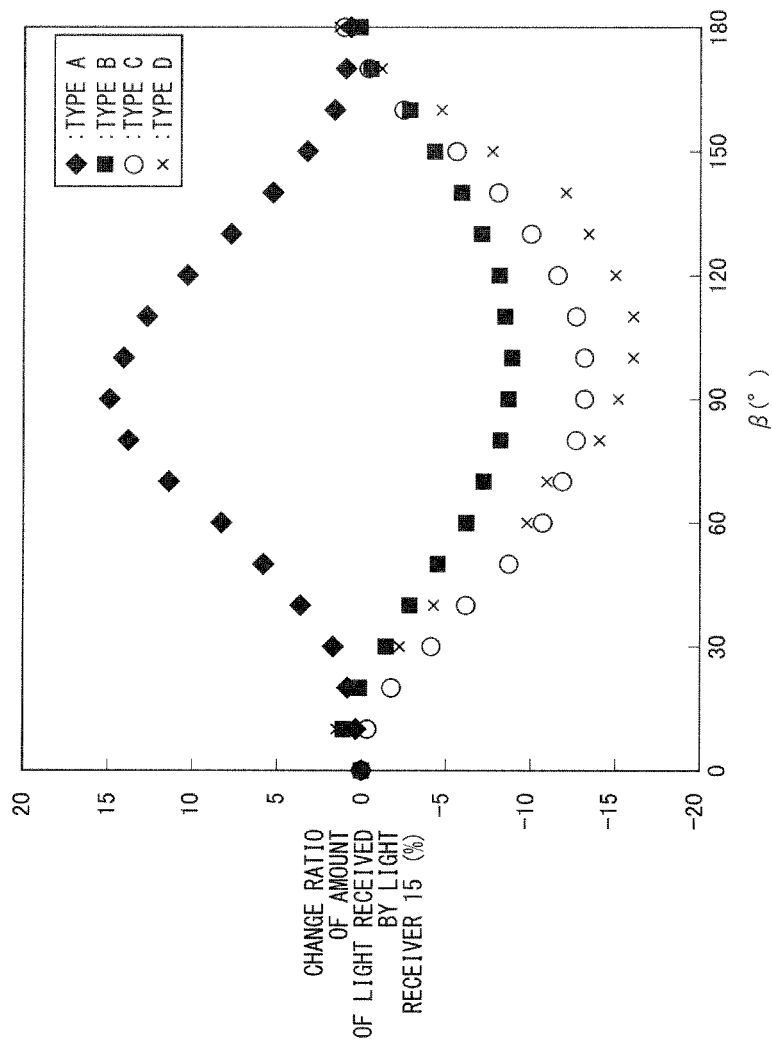
FIG. 23 provides a view illustrating a relationship between the angle β and a change ratio of the amount of light received by the light receiver 15.

In FIG. 23, regarding a plurality of recording paper each of a different brand, the relationship between the angle β and the change ratio of the amount of light received by the light receiver 15 is shown. The fibrous direction of brand A is parallel to the L direction. The fibrous directions of the brands B, C, and D are perpendicular to the L direction. According to FIG. 23, the amount of received light in brand A is at maximum when the angle β is about 90°. The amount of received light in each of the brands B, C and D is at minimum when the angle β is about 90°. This indicates that the diffuse reflectance on the surface of the recording paper M becomes the smallest when the incident surface is parallel to the fibrous direction, and the diffuse reflectance on the surface of the recording media becomes the largest when the incident surface is perpendicular to the fibrous direction.

In the present embodiment, the output level data of each brand includes the output level of each of the light receivers 13-15 when the incident surface is parallel to the L direction. The output level data of each brand also includes the output level of each of the light receivers 13-15 when the incident surface is perpendicular to the L direction. Therefore, both of the brand and fibrous direction of the recording paper M to be specified are obtained at the same time.

For example, in the first processing method, it can be determined that the fibrous direction is parallel to the L direction when the precision ratio RH is the largest, and determined that the fibrous direction of the recording paper M is perpendicular to the L direction when the precision ratio RV is the largest.

Similarly, in the second processing method, it can be determined that the fibrous direction of the recording paper M is parallel to the L direction when the precision ratio RH is the largest, and determined that the fibrous direction of the recording paper M is perpendicular to the L direction when the precision ratio RV is the largest.

In the third processing method, it can be determined that the fibrous direction of the recording paper M is parallel to the L direction when the precision ratio RH×RV is the largest, and determined that the fibrous direction of the recording paper M is perpendicular to the L direction when the precision ratio RH'×RV' is the largest.

As is obvious from the above description, in the color printer 2000 according to the present embodiment, the printer controller 2090 comprises the processing unit (processor) and controlling unit (controller), and the output level data of each brand which configures the database of the present invention.

As described above, the optical sensor 2245 according to the present embodiment includes the light source 10, the collimate lens 12, the three light receivers 13-15, the polarizing filter 16, the camera obscura 19 and so on.

Those components are arranged so that the light source 10 emits S polarized light, the light receiver 13 receives the surface-regular reflected light primarily, the light receiver 14 receives the P polarizing component which is included in the internal-diffuse reflected light, and the light receiver 15 receives the surface-diffuse reflected light primarily.

In the ROM of the printer controller 2090, the preliminary measured output levels of each of the light receivers 13-15 are stored as the output level data of each brand, when the optical sensor 2245 is at the first attitude or the second attitude. The output level of each of the light receivers 13-15 corresponds to the multiple types of the recording paper M whose brands are obvious.

The printer controller 2090 performs the paper-type specifying process to the recording paper M when the color printer 2000 is turned on or when the recording paper M is supplied to the paper-feed tray 2060. In the paper-type specifying process, after the recording paper M is illuminated by light from the light source 10 and the output levels of each of the light receivers 13-15 are determined, the printer controller 2090 refers to the output level data of each brand, calculates the precision ratio RH and precision ratio RV for each brand, and extracts the brand having the largest ratio in one of the above precision ratios as the brand of the recording paper M.

In this regard, the paper-type specifying process is performed to be more accurate than the conventional method because it is performed in view of the fibrous direction of the recording paper M. For reference, the fibrous direction has not been considered at all in the conventional paper-type specifying process.

In addition, in the present embodiment, the surface-emitting laser array is provided as the light source 10 so that the polarizing filter 16 which is to obtain linearly polarized illumination light is not necessary. Furthermore, in the surface-emitting laser array, it is possible to integrate multiple light-emitting parts with high density although it is difficult by the conventionally used LED and so on. In this case, a compact light source having a plurality of light-emitting parts can be obtained. In addition, because all of the laser beams can be concentrated around the optical axis of the collimate lens, multiple light can be nearly parallel light having a constant incident angle. In this case, a cost-saving collimate optical system can be provided. Therefore, a miniaturized and cost-saving optical sensor can be achieved.

In the printer controller 2090, the multiple light-emitting parts of the surface-emitting laser array are turned on at the same time. Therefore, it is possible to increase the amount of the P polarization component in the internal-diffuse reflected light.

Thus, the reflected light from the internal portion of the recording paper M can be separated with high accuracy by the optical sensor 2245. Compared with this, it has been difficult by the conventional sensor because the light is too weak to be separated. The reflected light from the inside portion of the recording paper M includes information regarding the internal condition of the recording paper M.

The printer controller 2090 specifies the brand of the recording paper M through the output signals of the three light receivers 13-15. That is, by considering the information regarding the internal condition of the recording paper M, the specifying level of the type of paper progresses. Thus, the printer controller 2090 can specify the type of the recording paper M at a high level such that it can specify the brand, which has been difficult to be specified by the conventional art.

A cost-saving and miniaturized optical sensor can be achieved because the components are configured simply without incorporating plural types of sensors.

According to the optical sensor 2245, the object can be detected with high accuracy with a simple configuration.

The color printer 2000 according to the present embodiment forms a high quality image consequently while avoiding the increase of cost and increase in size because it is provided with the optical sensor 2245. Furthermore, the conventional problems such as the settings needing to be input by hand or printing failure occurring by a setting mistake can be solved.

In the above-described embodiment, the four processing methods (first to fourth processing methods) are described as the paper-type specifying process but it is not limited to these.

Also, in the above-described embodiment, the case in which there are multiple detecting positions is described, but it is not limited to the above.

In the above-described embodiment, S1A, A2A, and S3A in the fourth processing method can be actual measured values. Similarly, values can be calculated using an approximate curve of a sine curve which approximates the relationship between the output levels of each of the light receivers 13-15 and the angle β.

In the above-described embodiment, the case in which the most suitable developing condition and transfer condition according to the brand of the recording paper M are set is described, but it is not limited to the above. The most suitable developing condition and transfer condition are determined according to at least one of the brand and fibrous direction of the recording paper M.

In addition, in the above-described embodiment, at least a part of the process according to the program through the CPU of the printer controller 2090 can be configured by hardware. Otherwise, all of the components can be configured by hardware.

In the above-described embodiment, the sensor-driving device 248 includes the base 2248*a*, the shaft 2248*b*, the guide 2248*c*, the first motor 2248*d*, the table 2248*e*, the table axis 2248*f*, and the second motor 2248*g*, but it is not limited to the above.

In the above-described embodiment, the light illuminating on the recording paper M is S polarized light, but it is not limited to the above. The illumination light on the recording paper M can be the P polarized light. However, in this regard, a polarizing filter which transmits S polarized light may be used instead of the polarizing filter 16, and the light receiver 14 receives the S polarizing component in the internal-diffuse reflected light.

Figure 24:
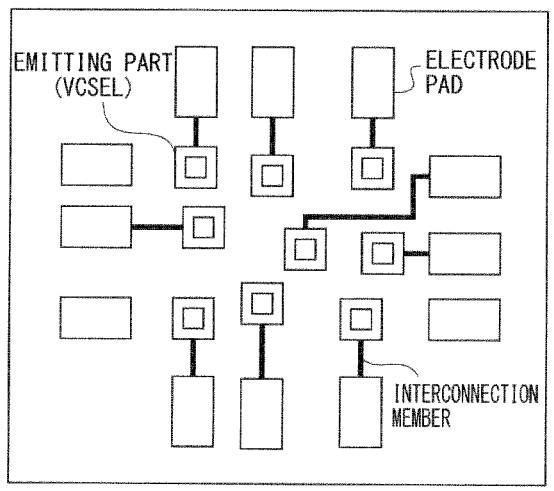
FIG. 24 provides a view illustrating a modified example of the surface-emitting laser array.

In addition, according to the above-described embodiment, the distance between at least a part of emitting parts in the plural emitting parts of the surface-emitting laser array can differ from the distance between the other emitting parts (refer to FIG. 24). That is, the distance between the emitting parts which are next to each other can be different.

In the above-described embodiment, the case in which the light source 10 includes the nine emitting parts is described, but it is not limited to the above.

Figure 25:
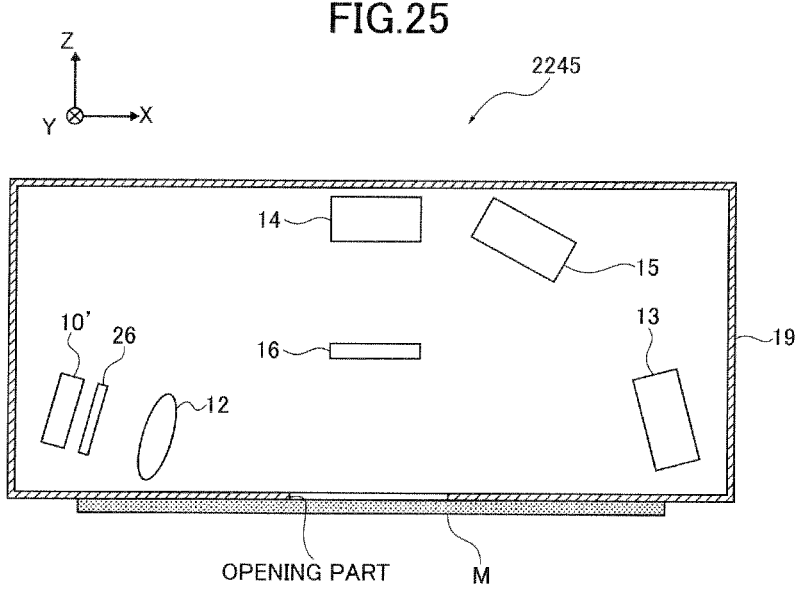
FIG. 25 provides a view illustrating a modified example of the optical sensor.

In the above-described embodiment, the case in which the light source 10 emits the linear polarized light is described, but it is not limited to the above. In this case, as shown in FIG. 25 as an example, a polarizing filter 26 through which the illumination light becomes S polarized light is required.

In addition, in the above-described embodiment, it is more preferable that a light concentrate lens be arranged in front of each of the light receivers 13-15. In this regard, the fluctuation of the amount of the light received by each of the light receivers 13-15 can be lowered.

In addition, in the above-described embodiment, the optical sensor 2245 can include a processor and perform a part of the process which may be performed by the printer controller 2090.

In addition, in the above-described embodiment, the case in which only one paper-feed tray is provided, but it is not limited to the above. A plurality of paper-feed trays can be disposed. In this regard, the optical sensor 2245 can be disposed for each of the paper-feed trays.

In addition, in the above-described embodiment, the brand of recording paper M can be specified while feeding. In this regard, the optical sensor 2245 is disposed adjacent to the feeding path of the recording paper M. For example, the optical sensor 2245 can be disposed adjacent to the paper-feeding path between the feeding roller 2054 and the transfer roller 2042.

In addition, the object to be specified by the optical sensor 2245 is not limited to the recording paper M.

Herein, in the above-described embodiment, the case in which the image-forming apparatus is the color printer 2000 is described, but it is not limited to the above. For example, a laser printer forming a monochrome image can be applied. Similarly, it can be an image-forming apparatus which is other than the printer, such as a copier, a facsimile, or a combined device having the above.

In addition, in the above-described embodiment, the case in which the image formation apparatus includes four photosensitive drums is described, but it is not limited to the above. For example, it can be a printer including five photosensitive drums.

In addition, in the above-described embodiment, the image-forming apparatus in which the toner image is transferred from the photosensitive drums through the transfer belt is described, but it is not limited to the above. It can be an image-forming apparatus in which a toner image is transferred directly to recording paper from a photosensitive drum.

In addition, the optical sensor 2245 can be applied to an image-forming apparatus which forms an image by spraying ink onto recording paper.

According to the optical sensor of the present invention, the object can be specified by a simple configuration with high accuracy.

Although the embodiments of the present invention have been described above, the present invention is not limited thereto. It should be appreciated that variations may be made in the embodiments described by persons skilled in the art without departing from the scope of the present invention.

The invention claimed is:

1. A sensor comprising:
   an optical sensor including a light source and a plurality of light receivers which receive light emitted from the light source and light regularly reflected and diffusely reflected by an object;
   a database including, for each object type amongst multiple known and different types of objects, (i) output data from the plurality of light receivers when an incident direction of the light emitted from the light source on an object of the object type forms a first direction in relation to the object of the object type and (ii) output data from the plurality of light receivers when the incident direction of the light emitted from the light source on the object of the object type forms a second direction which is orthogonal to the first direction; and
   a processor which controls the light emitted from the light source to illuminate an object of unknown type and specifies the type of the object by matching the output data of the plurality of light receivers to the database.

2. The sensor according to claim 1, wherein the light source illuminates the light from one of the first direction and second direction to the object of the unknown type.

3. The sensor according to claim 1, wherein the light source illuminates the light from both of the first direction and second direction to the object of the unknown type.

4. The sensor according to claim 1, wherein the processor calculates a precision ratio which represents a matching degree of the data of each types in the database and the output data of the light receiver in the case of the object of the unknown type, and determines the type of the object of the unknown type according to the precision ratio.

5. The sensor according to claim 1, wherein the processor obtains the output data of the plurality of light receivers by each of multiple positions of the unknown-type object on which the light from the light source illuminates.

6. The sensor according to claim 1, wherein the light source includes a surface-emitting laser array.

7. The sensor according to claim 1, wherein:
   the light source emits linearly polarized light having a first polarization direction;
   the optical sensor includes an optical element which is disposed on a path of the light diffusely reflected by the object on the incident surface of the object and transmits a linear polarizing component of a second polarization direction which is orthogonal to the first polarization direction; and
   the plurality of light receivers includes a first light receiver which is disposed on the path of the light regularly reflected on the object and a second light receiver which receives the light transmitted through the optical element.

8. The sensor according to claim 7, wherein the plurality of light receivers includes a third light receiver which is disposed on the path of the light diffusely reflected by the object on the incident surface of the object.

9. The sensor according to claim 1, wherein the light source illuminates the light from a third direction which is different from either of the first direction and second direction to the object of the unknown type.

10. The sensor according to claim 1, wherein the object is paper and the first direction is parallel to a fibrous direction of the paper.

11. An image-forming apparatus which forms an image on a recording media, comprising:
    the sensor according to claim 1 in which the recording media is the object; and
    a controller which controls an image-forming condition according to the specified result of the sensor.

12. The image-forming apparatus according to claim 11, wherein the recording media is paper and the first direction is parallel to a fibrous direction of the paper, and
    wherein the controller controls the image-forming condition according to at least one of a brand of the recording media and the fibrous direction.

13. A sensor comprising:
    an optical sensor including a light source and a plurality of light receivers which receive light emitted from the light source and light regularly reflected and diffusely reflected by an object;
    a database including output data regarding multiple objects of known and different types from the plurality of light receivers when an incident direction of light emitted from the light source forms a first direction to the object and when the incident direction of light emitted from the light source forms a second direction which is orthogonal to the first direction; and
    a processor which controls the light emitted from the light source to illuminate an object of unknown type and specifies the type of the object by matching the output data of the plurality of light receivers to the database,
    wherein the light source illuminates the light from a third direction which is different from either of the first direction and second direction to the object of the unknown type.

14. An image-forming apparatus which forms an image on a recording media, comprising:
    the sensor according to claim 13 in which the recording media is the object; and
    a controller which controls an image-forming condition according to the specified result of the sensor.

15. The image-forming apparatus according to claim 14, wherein the recording media is paper and the first direction is parallel to a fibrous direction of the paper, and
    wherein the controller controls the image-forming condition according to at least one of a brand of the recording media and the fibrous direction.

16. A sensor comprising:
    an optical sensor including a light source and a plurality of light receivers which receive light emitted from the light source and light regularly reflected and diffusely reflected by an object;
    a database including output data regarding multiple objects of known and different types from the plurality of light receivers when an incident direction of light emitted from the light source forms a first direction to the object and when the incident direction of light emitted from the light source forms a second direction which is orthogonal to the first direction; and
    a processor which controls the light emitted from the light source to illuminate an object of unknown type and specifies the type of the object by matching the output data of the plurality of light receivers to the database, wherein the object is paper and the first direction is parallel to a fibrous direction of the paper.

17. The sensor according to claim 16, wherein the processor calculates the fibrous direction of the object of the unknown type according to precision ratio which represents a matching degree of the data of each of the object types in the database and the output data of the light receivers for the object of the unknown type.

18. An image-forming apparatus which forms an image on a recording media, comprising:
   the sensor according to claim 16 in which the recording media is the object; and
   a controller which controls an image-forming condition according to the specified result of the sensor.

19. The image-forming apparatus according to claim 18, wherein the controller controls the image-forming condition according to at least one of a brand of the recording media and the fibrous direction.

\* \* \* \* \*